United States Patent
Wang et al.

(10) Patent No.: US 6,433,179 B1
(45) Date of Patent: *Aug. 13, 2002

(54) PROCESS FOR PRODUCING PAROXETINE

(75) Inventors: Shu-zhong Wang; Yasushi Matsumura, both of Yokohama (JP)

(73) Assignee: Asahi Glass Company Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/861,393

(22) Filed: May 21, 1997

(30) Foreign Application Priority Data

May 31, 1996 (JP) ............................. 8-139048

(51) Int. Cl.⁷ ................. C07D 405/12; A61K 31/445
(52) U.S. Cl. ................. 546/197; 546/282.7; 514/320; 514/338
(58) Field of Search .............. 546/197, 282.7; 514/338, 320

(56) References Cited

U.S. PATENT DOCUMENTS

| | | | |
|---|---|---|---|
| 3,912,743 A | 10/1975 | Christensen et al. | 514/321 |
| 4,007,196 A | 2/1977 | Christensen et al. | 514/321 |
| 4,268,515 A * | 5/1981 | Effland et al. | 514/287 |
| 4,282,233 A * | 8/1981 | Vilani | 546/93 |
| 4,721,723 A * | 1/1988 | Barnes | 514/321 |
| 4,985,446 A | 1/1991 | Drejer et al. | 514/321 |
| 5,227,379 A | 7/1993 | Jakobsen et al. | 514/228.2 |
| 5,461,050 A * | 10/1995 | Janssens | 514/214 |
| 5,672,612 A | 9/1997 | Ronsen et al. | 514/338 |

FOREIGN PATENT DOCUMENTS

| | | |
|---|---|---|
| EP | 0 190 496 | 8/1986 |
| EP | 0 223 403 | 5/1987 |
| EP | 812 827 | 12/1997 |
| JP | 6-47587 | 6/1994 |
| WO | WO 96/24595 | 8/1996 |

OTHER PUBLICATIONS

Muro et al. "Inverting steric configuration of aminoalcohols" CA 84:43593, 1974.*
Morrison and Boyd "organic Chemistry" Allyn and Bacon, pp. 298–301, 1973.*
Stemp et al. "Piperidine derivatives having gastrointestinal activity" CA 106:18361, see RN 105812–79–1 and RN 105812–85–9.*

* cited by examiner

*Primary Examiner*—Ceila Chang
(74) *Attorney, Agent, or Firm*—Oblon, Spivak, McClelland, Maier & Neustadt, P.C.

(57) ABSTRACT

A process for producing a paroxetine represented by the following formula (4), which comprises reacting an N-alkylpiperidine represented by the following general formula (1) with a haloformic acid ester represented by the general formula (2) to prepare an alkoxycarbonylpiperidine represented by the general formula (3), and hydrolyzing the alkoxycarbonylpiperidine under alkaline conditions:

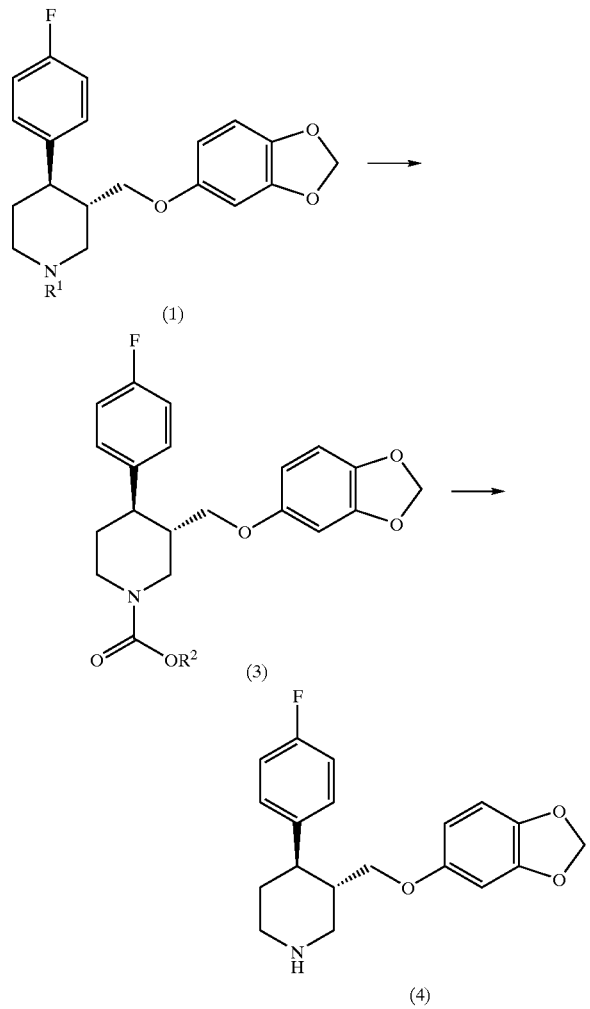

wherein each of $R^1$ and $R^2$ is a lower alkyl group, a lower cycloalkyl group, an aralkyl group or $C_mF_{2m+1}$ (wherein m is an integer of from 1 to 6), and X is a halogen atom.

11 Claims, No Drawings

PROCESS FOR PRODUCING PAROXETINE

The present invention relates to a process for producing paroxetine, which has an inhibitory action on 5-hydroxytryptamine (5-HT) and is useful as a therapeutic agent for various disease such as depression and Parkinson's disease.

Paroxetine is (3S, 4R)-3-[5-(1,3-dioxaindanyl)oxymethyl]-4-(p-fluorophenyl)piperidine represented by the after-mentioned formula (4).

As processes for producing paroxetine, the process of Christensen et al. (U.S. Pat. No. 4,007,196) and the process of Barnes et al. (Japanese Examined Patent Publication JP-B-6-47587) have been known. The former comprises reacting a N-methylpiperidine derivative represented by the after-mentioned general formula (1) (wherein $R^1$ is a methyl group) with phenyl chloroformate and hydrolyzing the resulting phenyl carbamate under alkaline conditions. The phenyl carbamate is different from compounds represented by the after-mentioned formula (3) only in that $R^2$ is a phenyl group. This process has drawbacks attributed to the low degree of conversion into the phenyl carbamate, that extra time and labor are required to separate the starting materials from the product, and that the ultimate yield by the process is low.

The latter process comprises converting a N-methylpiperidine derivative represented by the general formula (1) to a 1-chloroethyl carbamate represented by the following formula (5) and then hydrolyzing the 1-chloroethyl carbamate under acidic conditions. This process requires heating or stirring for a long time under acidic conditions, which may cause decomposition of the acetal moiety of the product. Prevention of contamination of an end product by the decomposition by-product requires much labor and cost which are greatly disadvantageous to production of medicines.

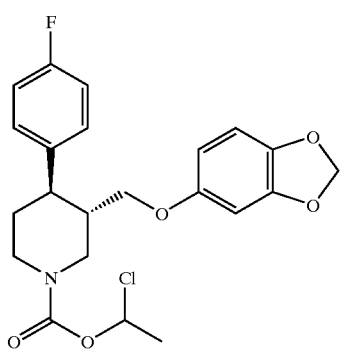

(5)

In order to solve the problems with the above-mentioned processes, the present invention provides: a process for producing paroxetine represented by the following formula (4), which comprises reacting an N-alkylpiperidine represented by the following general formula (1) with a haloformic acid ester represented by the general formula (3) to prepare an alkoxycarbonylpiperidine represented by the general formula (3), and hydrolyzing the alkoxycarbonylpiperidine under alkaline conditions:

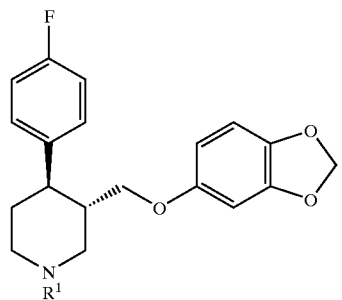

(1)

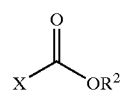

(2)

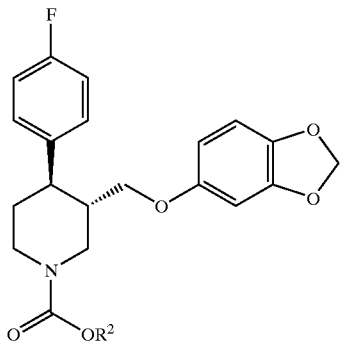

(3)

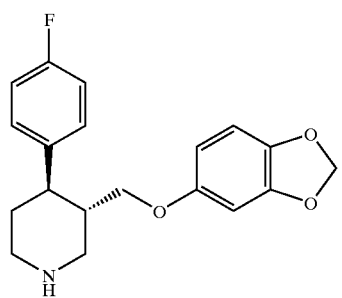

(4)

wherein each of $R^1$ and $R^2$ is a lower alkyl group, a lower cycloalkyl group, an aralkyl group or $C_mF_{2m+1}$ (wherein m is an integer of from 1 to 6), and X is a halogen atom.

Hereinabove and hereinafter, "lower" for an organic group means from 1 to 6 carbon atoms. Suitable examples of a "lower alkyl group" include a methyl group, an ethyl group, a propyl group, an isopropyl group, a butyl group, an isobutyl group, a t-butyl group, a pentyl group, a hexyl group and the like. A "lower cycloalkyl group" means a cycloalkyl group having from 3 to 6 carbon atoms on its ring, and its suitable examples include a cyclopropyl group, a cyclobutyl group, a cyclopentyl group and a cyclohexyl group.

An "aralkyl group" means an alkyl group substituted with an aryl group. An "aryl group", means a monovalent aromatic hydrocarbon group or a monovalent heterocyclic group and is preferably a phenyl group or its derivative or an oxygen-, nitrogen- or sulfur-containing 5- or 6-membered ring or a condensed heterocyclic ring derived therefrom. Suitable examples of an aryl group include a phenyl group, a tolyl group, a p-halphenyl group, a thiophenyl group, a pyrrolyl group, an imidazolyl group, a pyridyl group and an indolyl group. The alkyl moiety of an aralkyl group preferably has a carbon number of 4 or less. Suitable examples of an aralkyl group are a benzyl group, a benzhydryl group, a trityl group and a phenethyl group.

A "halogen atom" means a fluorine atom, a chlorine atom, a bromine atom or an iodine atom. $C_mF_{2m+1}$ means a perfluoroalkyl group, and m is preferably 1 or 2.

An N-alkylpiperidine represented by the general formula (1) as the starting material for the process of the present invention is obtainable by the process disclosed in U.S. Pat. No. 4,007,197. A haloformic acid ester represented by the general formula (2) is readily commercially available and also can be synthesized by known methods.

In order to carry out the process of the present invention, firstly, an N-alkylpiperidine represented by the general formula (1) [hereinafter referred to as a compound (1)] together with a haloformic acid esters represented by the general formula (2) [hereinafter referred to as a compound (2)] is stirred in an appropriate solvent in the presence or absence of an appropriate base at an appropriate temperature to prepare an alkoxycarbonylpiperidine represented by the general formula (3) [hereinafter referred to as a compound (3)].

The N-alkyl group moiety ($R^1$) of the compound (1) used here is preferably a lower alkyl group, more preferably a methyl group. The halogen atom (X) of the compound (2) used here is preferably a chlorine atom or a bromine atom, and particularly preferred is a chlorine atom. The alkyl moiety ($R^2$) of the compound (2) is preferably a lower alkyl group, more preferably a methyl group or an ethyl group.

The reaction temperature is preferably from 10 to 150° C., more preferably from 20 to 120° C. The amount of a compound (2) is preferably at least equivalent to, more preferably 1 to 10 times as many equivalents as the amount of the compound (1). The reaction is preferably carried out in the presence of a base so as to proceed satisfactorily.

Any aprotic solvents except for amines may be used in the above reaction, and when a base is present, a solvent resistant to the base is preferred. Suitable examples of the solvent are dichloromethane, chloroform, diethyl ether, t-butyl methyl ether, tetrahydrofuran, 1,4-dioxane, 1,2-dimethoxyethane, benzene, toluene, xylene, hexane, heptane, petroleum ether, methyl acetate, ethyl acetate, N,N-dimethylformamide and N,N-dimethylacetamide. Among them, aromatic solvents such as toluene and ethereal solvents such as tetrahydrofuran are particularly preferred.

The base used for this reaction maybe an organic amine, an alkoxide, an alkali metal hydroxide, an alkaline earth metal hydroxide, an alkali metal hydride, an alkaline earth metal hydride or a carbonic acid salt. Suitable examples of the base are 1,8-bis(N,N-dimethylamino)naphthalene, sodium methoxide, sodium ethoxide, sodium phenoxide, sodium hydroxide, potassium hydroxide, calcium hydroxide, magnesium hydroxide, sodium hydride, potassium hydride, calcium hydride, sodium carbonate, potassium carbonate, sodium hydrogencarbonate, potassium hydrogencarbonate, calcium carbonate and basic alumina. Metal hydrides are particularly preferred. The amount of the base is preferably at least equivalent to the amount of the haloformic acid ester used.

The finished reaction mixture is, concentrated, after filtration if the system contains any solid, to yield a compound (3).

Then, the compound (3) thus obtained is hydrolyzed in an appropriate solvent under alkaline conditions to yield paroxetine. The reaction temperature is preferably from 10 to 150° C., more preferably from 20 to 120° C.

In the hydrolysis, any solvent resistant to the hydrolytic conditions may be used. Suitable examples of the solvent are diethyl ether, t-butyl methyl ether, tetrahydrofuran, 1,4-dioxane, 1,2-dimethoxyethane, benzene, toluene, xylene, hexane, heptane, petroleum ether, methanol, ethanol, isopropanol, t-butanol, methyl cellosolve, ethyl cellosolve, water and mixtures of at least two of them.

The alkali which provides the alkaline conditions for the hydrolysis may be an alkoxide, an alkali metal hydroxide, an alkaline earth metal hydroxide or a carbonic acid salt. Suitable examples of the alkali are sodium methoxide, sodium ethoxide, sodium hydroxide, potassium hydroxide, calcium hydroxide, magnesium hydroxide, sodium carbonate, potassium carbonate, sodium hydrogencarbonate and calcium carbonate. Among them, metal hydroxides such as alkali metal hydroxides and alkaline earth metal hydroxides are particularly preferred. The alkali may be used in a catalytic amount in relation to the compound (3), but is preferably used in an amount at least equivalent to the compound (3).

From the finished reaction mixture, paroxetine can be obtained by extraction with an appropriate solvent such as toluene.

The compounds represented by the general formula (3) according to the present invention are novel compounds, and among them, those wherein $R^2$ is a lower alkyl group, especially a methyl group or an ethyl, group are especially useful.

Now, the present invention is described in further detail with reference to examples, but it should be understood that the present invention is by no means restricted to these specific examples.

COMPARATIVE EXAMPLE

To 343.4 mg (1 mmol) of (3S, 4R)-3-[5-(1,3-dioxaindanyl)oxymethyl]-4-(p-fluorophenyl)-1-methylpiperidine dissolved in 2.5 ml of dichloromethane, a solution of 144 µl of phenyl cloroformate dissolved in 1.5 ml of dichloromethane was added dropwise under cooling with ice, and the resulting mixture was stirred at room temperature for 6 hours, and after addition of 144 µl of phenyl chloroformate, stirred for 2 days. The reaction mixture was concentrated, and the resulting residue was analyzed by $^{19}$F-NMR and found to contain the above starting material and another material in a ratio of 1:1.

The above residue was partitioned between water and toluene. After the unreacted starting material was removed by washing with dilute hydrochloric acid, the toluene solution was dried and concentrated. The resulting residue was separated by silica gel column chromatography to obtain 149 mg (0.33 mmol) of (3S, 4R)-3-[5-(1,3-dioxaindanyl) oxymethyl]-4-(p-fluorophenyl)-1-phenoxycarbonylpiperidine.

$^1$H NMR(400 MHz, CDCl$_3$) δ 7.38(t, J=7.8 Hz, 2H); 7.15–7.24(m, 5H); 7.01(t, J=8.6 Hz, 2H); 6.64(d, J=8.3 Hz, 1H); 6.37(s, 1H); 6.16(d, J=6.8 Hz, 1H); 5.88(s, 2H); 4.63 (br, 1H); 4.47(br, 1H); 3.65(d, J=9.0 Hz, 1H); 3.50(dd, J=6.5, 9.3 Hz, 1H); 3.09(br, 1H); 2.99(br, 1H); 2.78(br, 1H); 2.15(br, 1H); 1.79–1.93(m, 2H). $^{19}$F NMR(376 MHz, CDCl$_3$, CFCl$_3$=0 ppm constant hereinafter) δ –116.4.

EXAMPLE 1

To 103.3 mg of (3S, 4R)-3-[5-(1,3-dioxaindanyl) oxymethyl]-4-(p-fluorophenyl)-1-methylpiperidine dissolved in 1 ml of dehydrated toluene, 12.6 mg of calcium hydride was added, and then a solution of 287 µl of ethyl chloroformate dissolved in 1 ml of dehydrated toluene was gradually added under cooling with ice. After 2.5 hours of stirring at room temperature, 10 mg of calcium hydride was added, and the reaction mixture was stirred overnight. Then, 200 μl of ethyl chloroformate was added, and the reaction mixture was stirred for one day. After addition of 170 mg of calcium hydride, the reaction mixture was stirred overnight.

The reaction mixture was filtered, and the filtrate was concentrated to give 111 mg of (3S, 4R)-3-[5-(1,3-dioxaindanyl)oxymethyl]-4-(p-fluorophenyl)-1-ethoxycarbonylpiperidine.

$^1$H NMR(400 MHz, CDCl$_3$) δ 7.11–7.18(m, 2H); 6.98(t, J=8.5 Hz, 2H); 6.63(d, J=8.3 Hz, 1H); 6.36(d, J=2.2 Hz, 1H); 6.15(d, J=8.3 Hz, 1H); 5.88(s, 2H); 4.48(br, 1H); 4.29(br, 1H); 4.18(q, J=6.8 Hz, 2H); 3.60(m, 1H); 3.46(m, 1H); 2.86(br, 2H); 2.70(br, 1H); 2.02(br, 1H); 1.6–1.9(m, 2H); 1.29(t, J=7.1 Hz, 3H). $^{19}$F NMR(376 MHz, CDCl$_3$) δ −116.6.

111 mg of the (3S, 4R)-3-[5-(1,3-dioxaindanyl)oxymethyl]-4-(p-fluorophenyl)-1-ethoxycarbonylpiperidine thus obtained was dissolved in 2 ml of toluene, and then 102 mg of potassium hydroxide and 1 ml of ethanol were added. The resulting mixture was refluxed under heating for 2 days and then concentrated. The resulting residue was diluted with water and extracted with toluene. The extract was dried and concentrated to give 62 mg of paroxetine.

$^1$H NMR(400 MHz, CDCl$_3$) a 7.16(dd, J=5.6, 8.3 Hz, 2H); 6.98(t, J=8.7 Hz, 2H); 6.61(d, J=8.3 Hz, 1H); 6.33(d, J=2.4 Hz, 1H); 6.12(dd, J=2.4, 8.3 Hz, 1H); 5.87(s, 2H); 3.56(dd, J=2.9, 9.5 Hz, 1H); 3.40–3.45(m, 2H); 3.18(d, J=12.0Hz, 1H); 2.64–2.77(m, 2H); 2.58(dt, J=3.9, 11.7 Hz, 1H); 2.05(m, 1H); 1.92(br, 1H); 1.66–1.83(m, 2H). $^{19}$F NMR(376 MHz, CDCl$_3$) δ −117.1.

EXAMPLE 2

To 142 mg of (3S, 4R)-3-[5-(1,3-dioxaindanyl)oxymethyl]-4-(p-fluorophenyl)-1-methylpiperidine dissolved in 2 ml of dehydrated toluene, a solution of 320 μl of methyl chloroformate in 1 ml of dehydrated toluene was gradually added under cooling with ice. The reaction mixture was stirred at room temperature overnight, and then, after addition of 265 mg of calcium hydride and 2 ml of dehydrated toluene, was further stirred for 4 hours. Then 160 μl of ethyl chloroformate was added, and the reaction mixture was stirred overnight.

The reaction mixture was filtered, and the filtrate was concentrated to give 69 mg of (3S, 4R)-3-[5-(1,3-dioxaindanyl)oxymethyl]-4-(p-fluorophenyl)-1-methoxycarbonylpiperidine.

$^1$H NMR(400 MHz, CDCl$_3$) δ 7.11–7.18(m, 2H); 6.97(t, J=8.7 Hz, 2H); 6.62(d, J=8.5 Hz, 1H); 6.35(d, J=2.5 Hz, 1H); 6.14(dd, J=2.4, 8.5 Hz, 1H); 5.87(s, 2H); 4.46(br, 1H); 4.29(br, 1H); 3.74(s, 3H); 3.58–3.61(m, 1H); 3.43–3.47(m, 1H); 2.6–2.9(br, 3H); 2.01(br, 1H); 1.66–1.85(m, 2H). $^{19}$F NMR(376 MHz, CDCl$_3$) δ −116.5.

69 mg of the (3S, 4R)-3-[5-(1,3-dioxaindanyl)oxymethyl]-4-(p-fluorophenyl)-1-methoxycarbonylpiperidine thus obtained was hydrolyzed in the same manner as in Example 1 to give 30 mg of paroxetine.

EXAMPLE 3

To 110 mg of (3S, 4R)-3-[5-(1,3-dioxaindanyl)oxymethyl]-4-(p-fluorophenyl)-1-methylpiperidine dissolved in 2 ml of dehydrated tetrahydrofuran, 192 mg of calcium hydride was added, and then 306 μl of ethyl chloroformate was gradually added under cooling with ice. The reaction mixture was stirred at room temperature overnight and heated on an oil bath at 70° C. for 7 hours. After gradual addition of ethanol, the reaction mixture was filtered, and the filtrate was concentrated to give 172 mg of oily (3S, 4R)-3-[5-(1,3-dioxaindanyl)oxymethyl]-4-(p-fluorophenyl)-1-ethoxycarbonylpiperidine.

172 mg of the oily (3S, 4R)-3-[5-(1,3-dioxaindanyl)oxymethyl]-4-(p-fluorophenyl)-1-ethoxycarbonylpiperidine thus obtained was dissolved in 4 ml of ethanol, and 330 mg of potassium hydroxide and 1 ml of water were added. The reaction mixture was heated on an oil bath at 90° C. for 3 days and then concentrated. The resulting residue was diluted with water and extracted with toluene, and the extract was dried and concentrated to give 70 mg of paroxetine.

EXAMPLE 4

To 1 g of (3S, 4R)-3-[5-(1,3-dioxaindanyl)oxymethyl]-4-(p-fluorophenyl)-1-methylpiperidine dissolved in 20 ml of dehydrated tetrahydrofuran, 2.87 ml of ethyl chloroformate was gradually added under cooling with ice. The reaction mixture was heated on an oil bath at 70° C. overnight, and then, after addition of 4.4 g of potassium carbonate, was heated for 2 days. After addition of ethanol, the reaction mixture was filtered. The filtrate was concentrated to give 1.22 g of oily (3S, 4R)-3-[5-(1,3-dioxaindanyl)oxymethyl]-4-(p-fluorophenyl)-1-ethoxycarbonylpiperidine.

1.22 g of the oily (3S, 4R)-3-[5-(1,3-dioxaindanyl)oxymethyl]-4-(p-fluorophenyl)-1-ethoxycarbonylpiperidine was hydrolyzed in the same manner as in Example 3, to give 780 mg of paroxetine.

EXAMPLE 5

To 102.6 mg of (3S, 4R)-3-[5-(1,3-dioxaindanyl)oxymethyl]-4-(p-fluorophenyl)-1-methylpiperidine dissolved in 2 ml of dehydrated toluene, 86 μl of ethyl chloroformate was added under cooling with ice, and the reaction mixture was stirred at room temperature for 2 days. The reaction mixture was concentrated to give 116 mg of an oily residue, and the residue was partitioned between water and toluene. After washed with dilute hydrochloric acid, the toluene solution was dried and concentrated to give 69 mg of (3S, 4R)-3-[5-(1,3-dioxaindanyl)oxymethyl]-4-(p-fluorophenyl)-1-ethoxycarbonylpiperidine.

69 mg of the (3S, 4R)-3-[5-(1,3-dioxaindanyl)oxymethyl]-4-(p-fluorophenyl)-1-ethoxycarbonylpiperidine thus obtained was hydrolyzed in the same manner as in Example 3 to give 27 mg of paroxetine.

It is possible to efficiently produce paroxetine, which is useful as a medicine, without formation of a decomposition by-product.

What is claimed is:

1. A process for producing a paroxetine represented by the following formula (4), which comprises reacting an N-alkylpiperidine represented by the following general formula (1) with a haloformic acid ester represented by the general formula (2) to prepare an alkoxycarbonylpiperidine represented by the general formula (3), and hydrolyzing the alkoxycarbonylpiperidine under alkaline conditions:

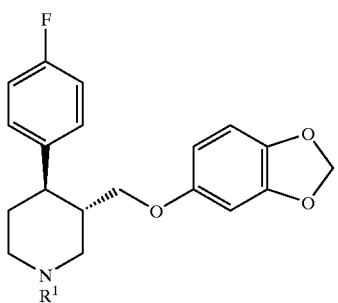

(1)

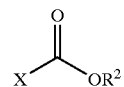

(2)

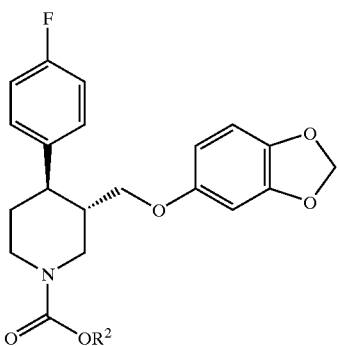

(3)

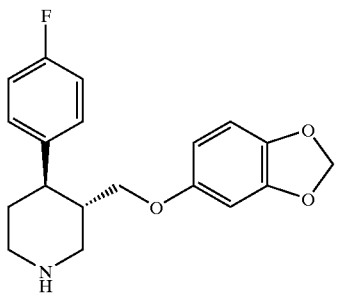

(4)

wherein R¹ is a lower alkyl group, R² is ethyl, X is a halogen atom, and the N-alkylpiperidine represented by general formula (1) has a (3S, 4R) configuration.

2. The process according to claim 1, wherein R¹ is a methyl group or an ethyl group.

3. The process according to claim 1, wherein R¹ is a methyl group.

4. The process according to claim 1, wherein X is a chlorine atom.

5. The process according to claim 1, wherein R¹ is a methyl group or an ethyl group, and X is a chlorine atom.

6. The process according to claim 1, wherein R¹ is a methyl group, and X is a chlorine atom.

7. The process according to claim 1, wherein the alkoxy-carbonylpiperidine represented by the general formula (3) is prepared by reacting the N-alkylpiperidine represented by the general formula (1) with the haloformic acid ester represented by the general formula (2) in the presence of a base.

8. The process according to claim 7, wherein the base is an alkali metal hydride, an alkaline earth metal hydride, or an alkali metal carbonate.

9. The process according to claim 7, wherein the reaction is carried out in a solvent at a temperature of from 10 to 150° C.

10. The process according to claim 1, wherein the alkoxy-carbonylpiperidine represented by the general formula (3) is hydrolyzed in a solvent at a temperature of from 10 to 150° C.

11. An alkoxycarbonylpiperidine represented by the following general formula (3):

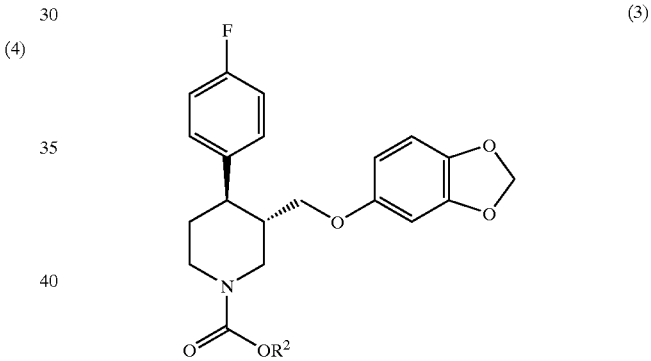

wherein R² is ethyl.

* * * * *